United States Patent
Wogritsch et al.

(10) Patent No.: US 11,828,692 B2
(45) Date of Patent: Nov. 28, 2023

(54) PREPARATION OF A SAMPLE FOR HIGH PRESSURE FREEZING

(71) Applicant: Leica Mikrosysteme GmbH, Vienna (AT)

(72) Inventors: Rainer Wogritsch, Vienna (AT); Paul Wurzinger, Deutsch-Wagram (AT)

(73) Assignee: Leica Mikrosysteme GmbH, Vienna (AT)

( * ) Notice: Subject to any disclaimer, the term of this patent is extended or adjusted under 35 U.S.C. 154(b) by 202 days.

(21) Appl. No.: 17/460,383

(22) Filed: Aug. 30, 2021

(65) Prior Publication Data
US 2022/0074834 A1    Mar. 10, 2022

(30) Foreign Application Priority Data
Sep. 4, 2020 (EP) .................................. 20194615

(51) Int. Cl.
    *G01N 1/42*     (2006.01)
    *F25D 3/10*     (2006.01)
    *C12M 1/00*    (2006.01)

(52) U.S. Cl.
CPC ................. *G01N 1/42* (2013.01); *F25D 3/10* (2013.01); *C12M 41/14* (2013.01); *F25D 2400/30* (2013.01)

(58) Field of Classification Search
CPC ......... G01N 1/42; F25D 3/10; F25D 2400/30; C12M 41/14; C12M 41/36; C12M 45/20
See application file for complete search history.

(56) References Cited

U.S. PATENT DOCUMENTS

| | | |
|---|---|---|
| 5,257,128 A | 10/1993 | Diller et al. |
| 2013/0227970 A1* | 9/2013 | Lihl .................... B29C 45/0053 62/62 |
| 2015/0125954 A1 | 5/2015 | Zimmermann et al. |
| 2018/0290144 A1 | 10/2018 | Lihl et al. |
| 2020/0041779 A1 | 2/2020 | Thomas et al. |
| 2020/0141846 A1 | 5/2020 | Zandbergen |

FOREIGN PATENT DOCUMENTS

| | | | |
|---|---|---|---|
| CN | 107003065 A | * 8/2017 | ........... A01N 1/0268 |
| DE | 202016007488 U1 | 3/2017 | |

OTHER PUBLICATIONS

Kaech, et al., "High-Pressure Freezing: Current State and Future Prospects", Chapter 8 of John Kuo (ed.), Electron Microscopy: Methods and Protocols, Methods in Molecular Biology, Jan. 2014, vol. 1117, pp. 151-171.

* cited by examiner

*Primary Examiner* — Emmanuel E Duke
(74) *Attorney, Agent, or Firm* — Hodgson Russ LLP

(57) ABSTRACT

A device for preparing a microscopic sample for a high-pressure freezing process in which the sample is provided using an arrangement having a middle plate of a high-pressure freezing cartridge and an incubation chamber, the middle plate being attached to and detachable from the incubation chamber by effecting a relative movement between the middle plate and the incubation chamber, and the sample being provided on an enclosing element which is fitted into an opening of the middle plate, wherein the device includes an engagement structure adapted to engage with the middle plate and to restrict a movement of the middle plate while the incubation chamber is moved, such as to effect the relative movement between the middle plate and the incubation chamber and to thereby detach the middle plate from the incubation chamber.

12 Claims, 8 Drawing Sheets

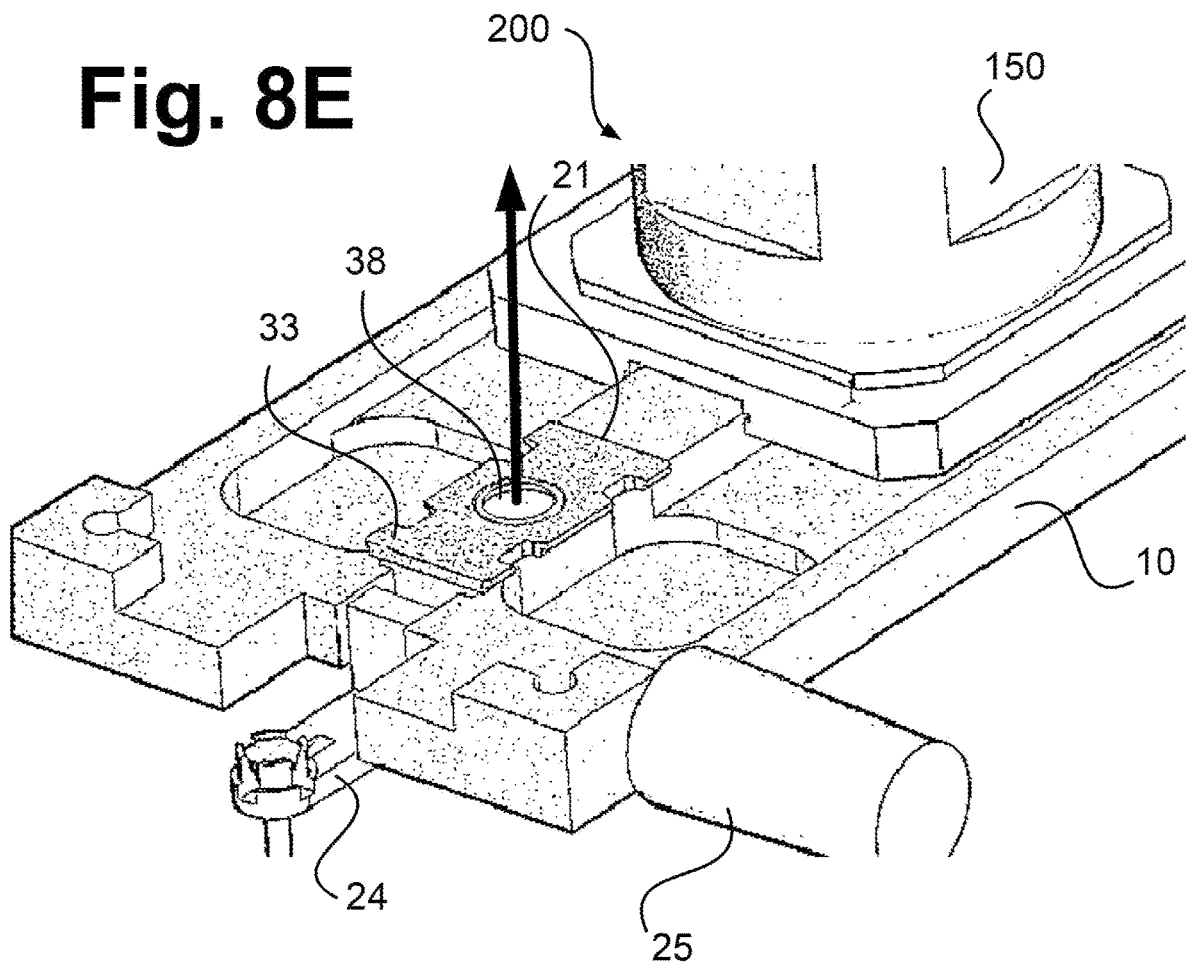

PREPARATION OF A SAMPLE FOR HIGH PRESSURE FREEZING

CROSS REFERENCE TO RELATED APPLICATIONS

This application claims priority of European patent application number 20194615.9 filed Sep. 4, 2020, the entire disclosure of which is incorporated by reference herein.

FIELD

The present disclosure relates to a device for preparing a microscopic sample for a high-pressure freezing process, to means usable in connection with such a device and to a corresponding method.

BACKGROUND

During imaging in a light microscope, living cells should be maintained at favorable environmental conditions. Stage incubators, stage heaters, carbon dioxide chambers and the like are common tools for this purpose.

There are several stage incubators and chambers for regulating the gas atmosphere around a sample during light microscopy available. The operating principle of a particular type of incubation chamber which offers the option to transfer samples between different locations while still maintaining the environmental conditions is disclosed in DE 20 2016 007 488 U1.

In FIG. 1 below, the assembly of such a type of incubation chamber is illustrated in a longitudinal section. The present disclosure is not limited to be used with any specific type of incubation chamber and FIG. 1 is provided for explanatory purposes only.

For assembling the incubation chamber 900 shown in FIG. 1, an open silicone cylinder 110 is mounted to a glass plate forming a bottom 120 of the incubation chamber. The cylinder 110 is closed by a glass lid 130 which may additionally be fixed with a metal ring 140. The whole assembly is then covered by a metal cover 150, for example made of aluminum, containing a glass window 160. The gas to which the sample is to be exposed is lead into the cover 150 through a feedthrough hole 170 or port connected to gas supply means. From there it maintains the atmosphere inside the chamber by diffusion through the silicone cylinder 110. As shown in FIG. 1, the incubation chamber 900 can be used to incubate a sample 1, such as a layer of cells, in a liquid medium 2.

It is often desired to arrest cell states observed in the light microscope, particularly in the incubation chambers just mentioned, as rapidly as possible, i.e. when detecting a physiological event, to preserve them for electron microscopical investigation. High pressure freezing is an adequate tool for sample fixation in this connection and is explained in more detail below. However, for this method the samples have to be contained in suitable sample holding means or carrier configurations for high pressure freezing devices typically referred to as "cartridges". The transfer into these cartridges is complicated and time consuming, especially when the sample is previously contained in an incubation chamber as mentioned. This is a major obstacle for the fast fixation of the cell state in the methods and arrangements of the prior art.

The present disclosure has the object of providing an advanced solution for high pressure freezing of samples held at defined environmental conditions in an incubation chamber.

SUMMARY

Against this background, the present disclosure proposes a device for preparing a microscopic sample for a high-pressure freezing process, means usable in connection with such a device and a corresponding method according to the independent claims. Preferred embodiments are the subject of the dependent claims and of the description that follows.

Hereinbelow, if reference is made to a device "for preparing" a microscopic sample for a high-pressure freezing process, this is intended to refer to a device adapted to perform at least one step of a method which, as a whole, prepares the sample for the high-pressure freezing process. The term "sample preparation", in this connection, is intended to also include the incubation of the sample, particularly in a defined atmosphere. The device must not necessarily be used for the whole procedure but can also be used for at least one step thereof, as each of the steps "prepares" the sample in some way for the high-pressure freezing process. The same applies when reference is made to a method.

Before turning to the features and specific advantages of the disclosure, some further details in connection with high pressure freezing and the problems of methods for transferring samples from incubation chambers into high pressure freezing devices will be presented for understanding the basis of the present disclosure.

Water is the most abundant cellular constituent and therefore important for preserving the cellular ultrastructure of biological samples. Currently the only way to fix cellular constituents without introducing significant structural alterations is by cryofixation. There are currently two common methods employed; plunge freezing and high pressure freezing. The present disclosure relates to high pressure freezing.

Cryofixation in general has two distinct advantages over chemical fixation. It is achieved within milliseconds and it ensures simultaneous immobilization of all macromolecular components. Many protein networks are very labile and fall apart with the slightest osmotic or temperature change and these unwanted effects are minimized during cryofixation. These techniques allow the study of biological samples with improved ultrastructural preservation and can facilitate the study of dynamic processes. Currently, the only method to vitrify thicker samples (up to 200 µm) is by high pressure freezing.

Successful cryofixation (vitrification) should result in the transformation of water from a liquid to an amorphous solid state without inducing the nucleation of ice crystals. The nucleation of ice crystals is dependent on temperature and pressure. Crystallization also depends on the cooling rates as freezing is a time dependent process. The cooling rates depend on the thermal properties of water, the sample thickness and the heat extraction flow at the surface of the specimen. High pressure freezing therefore is performed at high pressures and with a high flow of a refrigerant, particularly of liquid nitrogen.

For high pressure freezing, in other words, a biological sample is contacted at a high pressure with a refrigerant which is provided at a cryogenic temperature.

As biological or other aqueous preparations for high-pressure freezing typically or generally must generally not be thicker than 200 µm, the thickness of the samples must be limited. Furthermore, the samples must be protected against the flow of the cooling medium. For this purpose, cover elements consisting of metal sample carriers or sapphire plates or other suitable materials are placed at a defined distance from a sample carrier carrying the sample which can be, e.g., a sapphire plate. Currently, the carriers, intermediate and cover rings are manipulated with tweezers.

Devices for high pressure freezing of biological and industrial samples are marketed under the designations "EM ICE" and "EM HPM100" and "EM PACT" by Leica Microsystems. Such devices are described, for example, by A. Kaech and U. Ziegler, "High-Pressure Freezing: Current State and Future Prospects", chapter 8 of John Kuo (ed.), Electron Microscopy: Methods and Protocols, Methods in Molecular Biology, vol. 1117, 2014, DOI 10.1007/978-1-62703-776-1_8, pages 151 to 171.

With these devices, it is possible to cool a sample with liquid nitrogen at a pressure of up to 2,100 (two thousand one hundred) bar to a cryogenic temperature, which is in particular a temperature below 100° C., within a few milliseconds. In these devices, sample cartridges are, as mentioned, used to hold the sample during the high pressure freezing process. The sample cartridge may for example be made of high strength plastic and may comprise three components, namely two half cylinders with a channel adapted to be supplied with a stream of the refrigerant by the high pressure freezing device, and a sample holding arrangement, typically referred to as "middle plate", with an opening for holding the sample, the middle plate being sandwiched between the half cylinders. As mentioned, the present disclosure is not limited to a specific type of sample cartridge as long as this is compatible with the solution proposed by the present disclosure.

The sample itself is, in the middle plate, enclosed between two discs of a sufficiently thin and therefore thermally conductive material, e.g. sapphire, aluminum, or copper, within the opening of the middle plate, wherein the discs either themselves comprise recesses to receive the sample or are separated by spacer rings to form a retainer for the sample. The pressure at the location of the sample is generated by the refrigerant which is pressurized to e.g. 2,100 bar for this purpose. Further details in this connection are explained with reference to the figures hereinbelow. If reference is made to a "middle plate" hereinbelow, this is intended to refer to a generally flat element, or arrangement of elements adapted to provide a space receiving a sample to be vitrified. Particularly, the middle plate is, in an assembled state, composed at least of a generally flat structure with an opening in which suitable discs may be arranged to form the sample space. These discs can be formed of various materials and need not be transparent. The term "middle plate" can, at any occurrences used, be replaced by "carrier element".

The incubation chambers which are used to maintain physiologically favorable environmental conditions and which were described at the outset are designed for glass slides or cover glasses as standard sample carriers. Therefore, a high-pressure freezing of samples contained in such incubation chambers would have to include a transfer of the sample to the middle plate of a high-pressure freezing cartridge. This obviously is connected with a disturbance of the environmental conditions to which the sample is exposed in the incubation chamber and could generate unwanted physiological reactions. Furthermore, such a step is time-consuming and therefore could result in an unwanted time lag which could make the observation of rapid physiological changes impossible.

One aspect of the present disclosure therefore relates to an advantageous solution in which a middle plate of a high-pressure freezing cartridge is, in an opened state, mounted at the bottom of an incubation chamber of the type described above. An "opened state" of the middle plate is to be understood as a state in which one of the discs referred to above, and termed "enclosing element" hereinbelow, is mounted within the opening of the middle plate while the other one is not yet mounted there. The sample, which is placed on the disc already mounted can therefore be taken from the incubation chamber and can be, after the other disc is mounted in order to close and seal the sample space, directly and rapidly be transferred, together with the other parts of the high-pressure freezing cartridge, to a high-pressure freezing device.

A further aspect of the present disclosure relates to the step of removing the middle plate from the incubation chamber to which it is mounted at the bottom. Such a detachment and transfer would, in arrangements not designed according to the present disclosure, require many manual steps, which are correspondingly time-consuming. The disclosure solves this problem by separating the middle plate together with the sample from the incubation chamber by a simple movement wherein the middle plate is held fixed by a temporary holding structure. Once detached, the middle plate can be located in the immediate vicinity of a loading area of a high-pressure freezing device or even in a dedicated loading station thereof.

Said closing the middle plate, or more specifically, its sample space, which includes carefully fitting the other disc into the opening forming the sample space and optionally also fitting spacer and gasket rings, requires skill and involves several manipulation steps and is therefore time-consuming in conventional methods. An important aspect of the disclosure therefore relates to a device which includes placing the middle plate in its opened state at a geometrically well-defined position and placing the other disc, which preferably may be a single metal element, quickly and safely into the opening with the aid of a swivel arm.

Features and Advantages

According to the present disclosure, a device for preparing a microscopic sample for a high-pressure freezing process is proposed. The device provided according to the present disclosure can be a high-pressure freezing device adapted to perform all or at least a part of the further steps of high-pressure freezing as well, and therefore may also comprise a so-called "loading station" adapted to assemble a high-pressure freezing cartridge, e.g. as shown in FIGS. 2 and 3 below, and insert this cartridge into a space or chamber wherein a high-pressure refrigerant is passed through the cartridge. The device may also include the means for providing and passing the high-pressure refrigerant through the chamber. The device can thus comprise all or a subset of the means used for high-pressure freezing processes according to the prior art or expert literature, such as Kaech and Ziegler (see above). However, the device provided according to the present disclosure may also be a dedicated device separate from a high-pressure freezing device, i.e. as a separate constructional unit, and may contain exactly the components described hereinbelow and optionally further components. In the latter case, the dedicated device may e.g. be placed in close proximity of the high-pressure freezing device.

According to the present disclosure, the device is used in connection with an incubation of the sample in an incubation chamber already described at the outset, or a similar type of incubation chamber. According to the present disclosure, as previously more generally stated in connection with the essential or important aspects of the disclosure, the sample is provided using an arrangement comprising a middle plate of a high-pressure freezing cartridge and such an incubation chamber, wherein the middle plate is attached to the incubation chamber. According to the present disclosure, therefore, a laborious transfer of the sample to the middle plate of a high-pressure freezing cartridge, which would be necessary when using set-ups according to the prior art, is no longer required. This significantly reduces the disturbance of the environmental conditions to which the sample is exposed in the incubation chamber and reduces or avoids unwanted physiological reactions. According to the present disclosure, as the sample may already be provided on a corresponding middle plate, time lags between incubation and high-pressure freezing are also reduced such that also specific points of rapid physiological changes may be observed.

In the context of the present disclosure, the middle plate is attached to the incubation chamber such as to be detachable from the incubation chamber by effecting a relative movement between the middle plate and the incubation chamber, as described in further detail below. Such a detachment according to the present disclosure, effected by a simple movement wherein the middle plate is held fixed by a holding structure termed "engagement structure" in the following, reduces time and effort of separating the incubation chamber and the middle plate, such that the latter can be transferred particularly rapidly to a high-pressure freezing device. Once detached, the middle plate can be located in the immediate vicinity of a loading area of a high-pressure freezing device or even in a dedicated loading station thereof, or the detachment can be effected in a structure or apparatus part which is positioned in immediate vicinity of, or is a part of, a high-pressure freezing device.

The middle plate of the high-pressure freezing cartridge is, in the context of the present disclosure, mounted at the bottom of an incubation chamber of the type described above in an opened state, as mentioned. That is, the sample is provided on an enclosing element which is fitted into an opening of the middle plate. Preparing the middle plate for the assembly of a high-pressure freezing cartridge thus essentially only requires inserting a further enclosure element in order to seal the sample, which may be effected in a device according to a particularly preferred embodiment of the present disclosure as described below.

The device provided according to the present disclosure, as mentioned, comprises an engagement structure adapted to engage with the middle plate and to restrict a movement of the middle plate while the incubation chamber is moved, such as to effect said relative movement between the middle plate and the incubation chamber and to thereby detach the middle plate from the incubation chamber. Particularly, the engagement structure may be provided such that the incubation chamber with the middle plate attached thereto can be positioned by hand whereby the middle plate as a whole, or a structure thereof, is inserted at least in part in the engagement structure or contacts the same. By a simple movement of the incubation chamber, preferably also effected by hand, the middle plate can be detached therefrom, remaining to be being inserted at least in part in the engagement structure or contacting the same.

According to a particularly preferred embodiment of the present disclosure, which was already briefly discussed above, the device provided according to the present disclosure is adapted to hold the middle plate detached from the incubation chamber in place at a processing position. Such a position may particularly be defined by the engagement structure used for detaching the middle plate from the incubation chamber or further positioning elements such as stops, fences, recesses, frames and the like. The device comprises a pivoting arm with a receptacle adapted to receive a further enclosing element to be fitted into the opening of the middle plate, such as to enclose the sample therein. The pivoting arm serves, in this embodiment, as a means to precisely position the enclosing element with which the sample is sealed in the opening of the middle plate, thus eliminating or significantly reducing the skill conventionally needed in this connection.

In the present disclosure, also the number of spacer and gasket rings to be fitted in the opening of the enclosing element may be reduced, or such elements can be completely dispensed of, thus further reducing the time and effort of sample preparation for cryofixation. This may be the result of the pivoting arm provided according to the present disclosure which may allow adapted enclosing elements to be used which can be press-fitted without gaskets into the opening of the middle plate, as would not be possible by hand, using tweezers. At least one of the enclosing elements may, in order to reduce the need for spacers, be provided with a recess forming a sample chamber or, expressed in other terms, an outer ring protruding from a surface of the enclosing element.

For the purposes mentioned, and to provide the advantages of the present disclosure just discussed, in the preferred embodiment of the present disclosure just discussed the pivoting arm is pivotable between a loading position wherein the further enclosing element is insertable into the receptacle of the pivoting arm and an inserting position in which the further enclosing element in the receptacle of the pivoting arm is placed in the opening of the middle plate held in place at the processing position.

In a first group of embodiments of the present disclosure, the middle plate of the high-pressure freezing cartridge is attached to a lower surface of the bottom of the incubation chamber by using at least one of mechanical and magnetic attachment means, such as magnets inserted into the bottom of the incubation chamber, brackets, clamps and the like. In this first group of embodiments, the bottom of the incubation chamber is provided with an opening which provides access to the opening in the middle plate, but which itself is not used in attaching the middle plate. An upper surface of the middle plate is, in this embodiment, directly attached to the lower surface of the incubation chamber. Sealing elements like a sealing ring may be provided between the two surfaces in order to avoid leakage of incubation liquid from the incubation chamber.

In the first group of embodiments, the middle plate is detachable from the incubation chamber by effecting said movement in the form of at least one of a linear and/or a rotational movement of the incubation chamber in a plane corresponding to the lower surface of the bottom of the incubation chamber, a tilting movement of the incubation chamber around an axis which is parallel to the lower surface of the bottom of the incubation chamber and a lifting movement of the incubation chamber in a direction at an angle to the lower surface of the bottom of the incubation chamber, and the engagement structure is particularly adapted to engage with the middle plate to restrict said at least one of a linear, rotational, tilting and lifting movement.

To restrict a linear movement, a simple stop or fence can be provided as the engagement structure such that, when the middle plate is attached to the bottom surface of the incubation chamber and protrudes therefrom, it can be withheld from movement when the incubation chamber is pushed over the stop or fence and stays at a position defined by the stop or fence. In such a configuration, the means for attachment of the middle plate to the incubation chamber are designed such as to provide an attachment force that can be overcome by a corresponding pushing force, e.g. as effected by hand.

To restrict a rotational movement, a recess or at least two fences may be provided as the engagement structure into or between which the middle plate attached to the bottom surface of the incubation chamber and protruding therefrom fits. Rotating the incubation chamber thus detaches the middle plate attached to the bottom surface of the incubation chamber therefrom. Again, the means for attachment of the middle plate to the incubation chamber are, in this connection, designed such as to provide an attachment force that can be overcome by a corresponding rotational force, e.g. as effected by hand.

In this case, one or more, particularly two, protrusions, particularly in the form of tenons or pins can be provided as the engagement structure(s), as additional engagement structure(s), or as alignment structure(s) additional to the engagement structure(s). The one or more protrusions may be provided at the middle plate and at least one matching recess may be provided at a counterpart thereof with which the incubation chamber is brought into contact for the detachment of the middle plate, or the one or more protrusions may be provided at the counterpart and at least one matching recess may be provided at the middle plate.

In order to restrict a tilting movement, the engagement structure may be provided as a structure with an undercut into which a corresponding protrusion provided at the middle plate may be inserted, such that when tilting the incubation chamber while maintaining an insertion of the protrusion of the middle plate into the undercut an overhang of the undercut "pulls off" the middle plate from the incubation chamber in a manner similar to a cap lifter or bottle opener. The insertion of the protrusion of the middle plate into the undercut may be maintained by pressing the incubation chamber with the middle plate by hand into a direction of the undercut or by providing a stop restricting movement out of the undercut. Also here, the means for attachment of the middle plate to the incubation chamber are, in this connection, designed such as to provide an attachment force that can be overcome by a corresponding tilting force, e.g. as effected by hand.

A lifting movement may be restricted by providing a parallel set of guiding elements with undercuts, e.g. in the form of a dovetail guide, which are adapted to slidingly receive complementary structures provided at the middle plate in an insertion direction. When lifting the incubation chamber in a direction at an angle to the insertion direction, and when selecting suitable attachment forces here as well, the middle plate may thus be detached from the incubation chamber.

It should be understood that in the present disclosure, in the first set of embodiments, the movement or trajectories of movement are not necessarily restricted to either one of a linear, a rotational, a tilting and a lifting movement, but e.g. a rotational movement or a linear movement may be followed by a lifting movement, etc.

In general, in the first set of embodiments, the middle plate may protrude from the bottom of the incubation chamber when attached thereto. The engagement structure may be provided as a recess with a shape complementary to at least a part of a shape of the middle plate and adapted to receive at least a part of the middle plate protruding from the bottom of the incubation chamber. The term "recess", in this connection, shall be understood broadly and may be a recess in a flat surface, between fencing structures or in front of a stop, an undercut of a guiding rail or a different structure, etc.

In a second set of embodiments of the present disclosure, a bottom of the incubation chamber comprises an opening with a guiding structure adapted to slidingly receive the middle plate. That is, in contrast to the first set of embodiments just discussed, the opening not only provides an access to the opening in the middle plate, but also serves as an attachment structure. The guiding structure adapted to slidingly receive the middle plate may particularly be designed as a set of dovetail guides, designed to mate with corresponding structures in the middle plate. In this second set of embodiments, the middle plate is detachable from the incubation chamber by effecting said movement in the form of a linear movement defined by said guiding structure and the engagement structure comprises a stop to hold the middle plate in place while effecting said movement. In other words, the middle plate may be pushed out of the guiding structure such as a dovetail guide by such a movement. Also in this case, additional protrusions and recesses as described before can be provided.

In the embodiment of the present disclosure where a pivoting arm is provided which is adapted to put the enclosing element in place, the receptacle may be adapted to adhesively hold the further enclosing element, in order to avoid a displacement or falling out during the pivoting movement of the pivoting arm. An adhesive force is selected such that it may be overcome by a holding force with which the further enclosing element is held in the opening of the middle plate after being inserted, e.g. in the form of a press fit.

The present disclosure also relates to an incubation chamber adapted to be used in an arrangement comprising the incubation chamber and a middle plate of a high-pressure freezing cartridge, the incubation chamber comprising means to attach the middle plate to the incubation chamber such that the middle plate is detachable from the incubation chamber by effecting a relative movement between the middle plate and the incubation chamber. As to such an incubation chamber and the specific features and advantages thereof, reference is made to the explanations above. Each and any feature described hereinabove may be part of the incubation chamber provided according to the present disclosure.

Also a middle plate of a high-pressure freezing cartridge, i.e. a sample holding means for high-pressure freezing, adapted to be used in an arrangement comprising an incubation chamber and the middle plate is part of the present disclosure. The middle plate provided according to the present disclosure comprises means to attach the middle plate to the incubation chamber such that the middle plate is detachable from the incubation chamber by effecting a relative movement between the middle plate and the incubation chamber. Also for the middle plate and the specific features and advantages thereof, reference is made to the explanations above. Each and any feature described hereinabove may be part of the middle plate provided according to the present disclosure.

According to a particularly preferred embodiment of the present disclosure, an incubation chamber may be manufactured together with the middle plate in a suitable process, particularly pressure molding or additive manufacturing (3D printing) wherein breakable connections between the incubation chamber and the middle plate are provided in the form of thin, weak or brittle structures forming intentional breaking points. By destroying these structures, essentially as described before, i.e. using an engagement structure, the middle plate can be detached from the incubation chamber.

The explanations above equally apply to an arrangement comprising an incubation chamber and a middle plate of a high-pressure freezing cartridge which is provided according to the present disclosure.

The method provided according to the present disclosure is provided for preparing a microscopic sample for a high-pressure freezing process in which the sample is provided using an arrangement comprising a middle plate of a high-pressure freezing cartridge and an incubation chamber, the middle plate being attached to the incubation chamber and being detachable from the incubation chamber by effecting a relative movement between the middle plate and the incubation chamber, and the sample being provided on an enclosing element which is fitted into an opening of the middle plate. The method provided according to the present disclosure comprises using a device comprising an engagement structure adapted to engage with the middle plate and to restrict a movement of the middle plate while the incubation chamber is moved, and the method comprises effecting an engagement of the engagement structure with the middle plate and effecting said relative movement between the middle plate and the incubation chamber, thereby detaching the middle plate from the incubation chamber.

Also in connection with the method provided according to the present disclosure, reference is made to the explanations above. The method provided according to the present disclosure takes profit of the features and advantages of the device and further elements and arrangements described above in preferred embodiments.

In a particularly preferred embodiment of the method provided according to the present disclosure, said device is adapted to hold the middle plate detached from the incubation chamber in place at a processing position, and the device comprises a pivoting arm with a receptacle adapted to receive a further enclosing element to be fitted into the opening of the middle plate, in order to enclose the sample, wherein the pivoting arm is pivotable between a loading position wherein the further enclosing element is insertable into the receptacle of the pivoting arm and an inserting position wherein the further enclosing element inserted in the receptacle of the pivoting arm is placeable in the opening of the middle plate held in place at the processing position. The method comprises holding the middle plate detached from the incubation chamber in place at the processing position and inserting the further enclosing element using the pivoting arm of the device.

In any case, in the method provided according to the present disclosure a device, an incubation chamber, a middle plate and/or an arrangement as described in different embodiments before may be used.

In the method according to the present disclosure, providing the sample may include exposing living matter to defined environmental conditions provided in the incubation chamber, as generally known for such incubation chambers.

BRIEF DESCRIPTION OF THE DRAWING VIEWS

Further features of the present disclosure will be described in connection with the appended drawings in which embodiments of the disclosure are described vis-à-vis the prior art. Be it noted that specific features of the embodiments described in connection with the drawings and described above can be used in any combination and/or isolatedly without leaving the scope of the disclosure.

FIGS. 8A to 8E illustrate steps of detaching a middle plate from an incubation chamber by sliding and sealing an opening according to an embodiment of the present disclosure.

In the Figures, like elements are indicated with identical reference numerals. Repeated explanations thereof are omitted for reasons of conciseness only.

DETAILED DESCRIPTION

Figure 1:
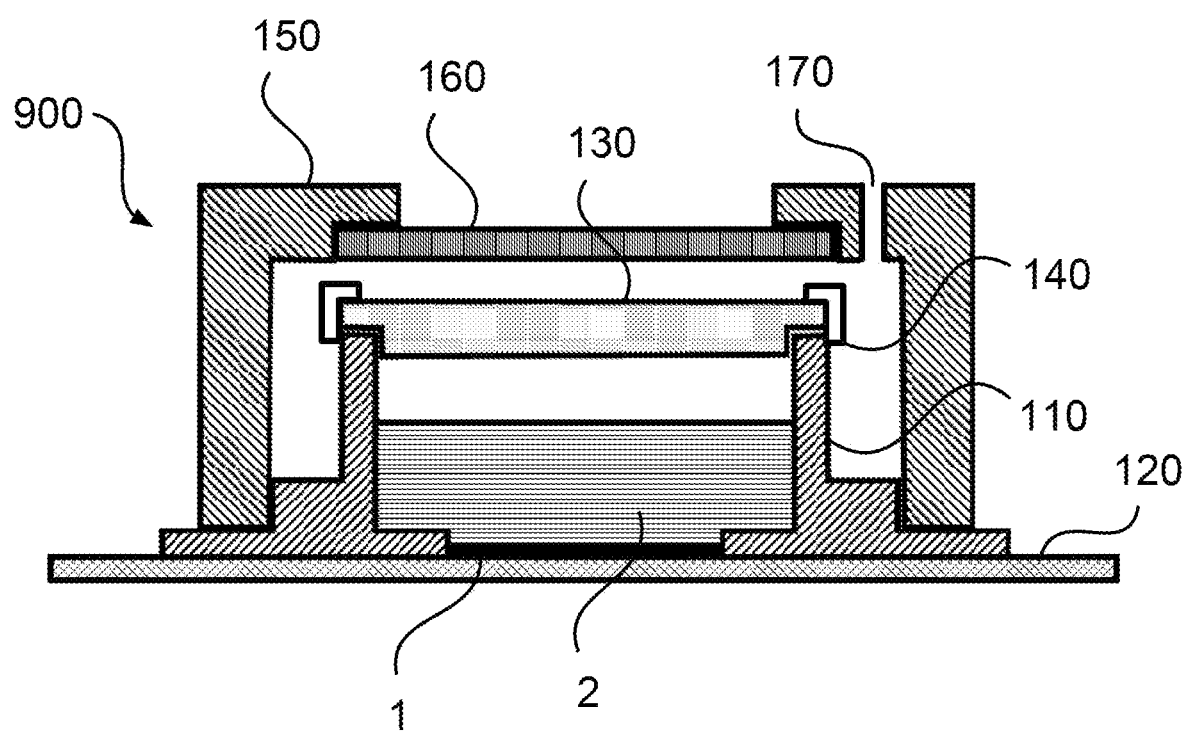
FIG. 1 illustrates an incubation chamber for incubating a sample not forming part of the present disclosure in a simplified sectional view.

FIG. 1 shows an incubation chamber 900 for incubating a sample not forming part of the present disclosure in a simplified sectional view and was already explained at the outset. Reference is made to the explanations above. Again, it is to be pointed out that the present disclosure is not intended to be limited by the specific type of incubation chamber shown here.

Figure 2:
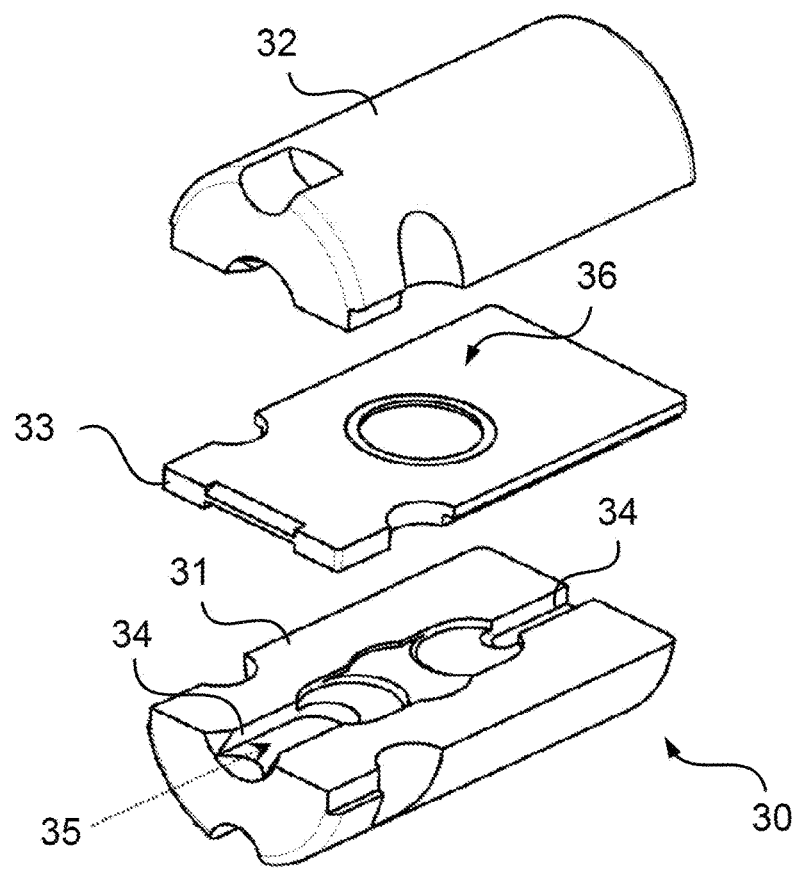
FIG. 2 illustrates a high-pressure freezing cartridge usable in connection with the present disclosure in a simplified exploded view.

FIG. 2 shows a high-pressure freezing cartridge 30, i.e. a sample holding means, which may be used in connection with the present disclosure in an exploded view. The cartridge 30 can be used in high-pressure freezing devices generally known from the art which were referred to above. Reference is made, for example, to the literature cited above for the "EM ICE" "EM HPM100" and "EM PACT" systems by Leica Microsystems, e.g. to DE 10 2013 003 164 A1 which further describes details of a high pressure freezing system, and to scientific review literature such as Kaech & Ziegler (see above). The cartridge 30 can, in an assembled state, be transferred into the high-pressure freezing device by using a known holder. Handling of cartridges such as the cartridge 30 is extensively described elsewhere and will not be explained here for reasons of conciseness.

The cartridge 30 comprises two holding elements 31, 32, each essentially of a half cylindrical shape. A middle plate 33 is arranged between the holding elements 31, 32 of the cartridge 30. The holding elements 31, 32 provide refrigerant channels 34 therebetween, the refrigerant channels 34 being formed by grooves along the longitudinal direction on the inner flat surfaces of the holding elements 31, 32. Through the refrigerant channels 34, a cryogenic refrigerant can be passed to a sample received or contained in the middle plate 33 in an opening 36 forming a sample space, essentially along the longitudinal axis of the cartridge 30 and in the direction of the dotted arrow 35 as illustrated in FIG. 2.

Figure 3:
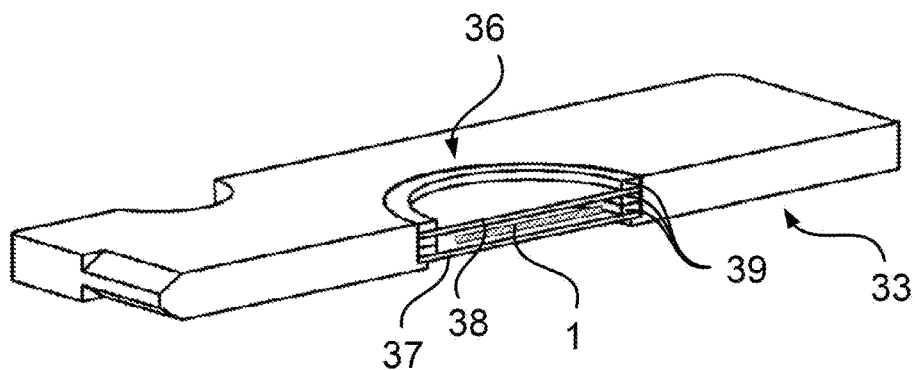
FIG. 3 illustrates a middle plate of a high-pressure freezing cartridge usable in connection with the present disclosure in a simplified sectional view.

FIG. 3 shows the middle plate 33 which is used in the cartridge 30 as shown in FIG. 2 in a longitudinal section along a vertical plane, so that the sample space formed in the opening 36 such as according to FIG. 1 is shown cut open. The opening 36 is of a circular shape and is arranged in or near to the center of the middle plate 33 and the sample 1 is held between two enclosing discs including a first (bottom) disc 37 and a second (top) disc 38, e.g. circular enclosing elements 37, 38 in the form of discs made of sapphire, metal or another suitable material. The enclosing elements 37, 38 are fixed in the opening 36 and their distance is adjusted by fixing, gasketing and/or spacer means 39. The enclosing elements 37, 38 themselves may also comprise one or more recesses in which the sample 1 can be received when they are inserted into the opening 36, thereby reducing or eliminating the need for fixing, gasketing and/or spacer means 39. The enclosing elements 37, 38 also serve to protect the sample 1 since the rapid flow of refrigerant required for cooling would otherwise carry away the sample.

Further details and variants of a cartridge 30 and its middle plate 33 are described in the prior art mentioned. Again, it should be understood that the present disclosure is not limited to the specific configuration of the cartridge 30 and the middle plate 33. The entire cartridge 30 is dimensioned in such a way that the high pressures (e.g. above 2,000 bar) required for high pressure freezing can be built up and be maintained within a period of preferably 200 to 500 ms, whereby rapid freezing of sample 1 is achieved within this time interval.

Figure 4:
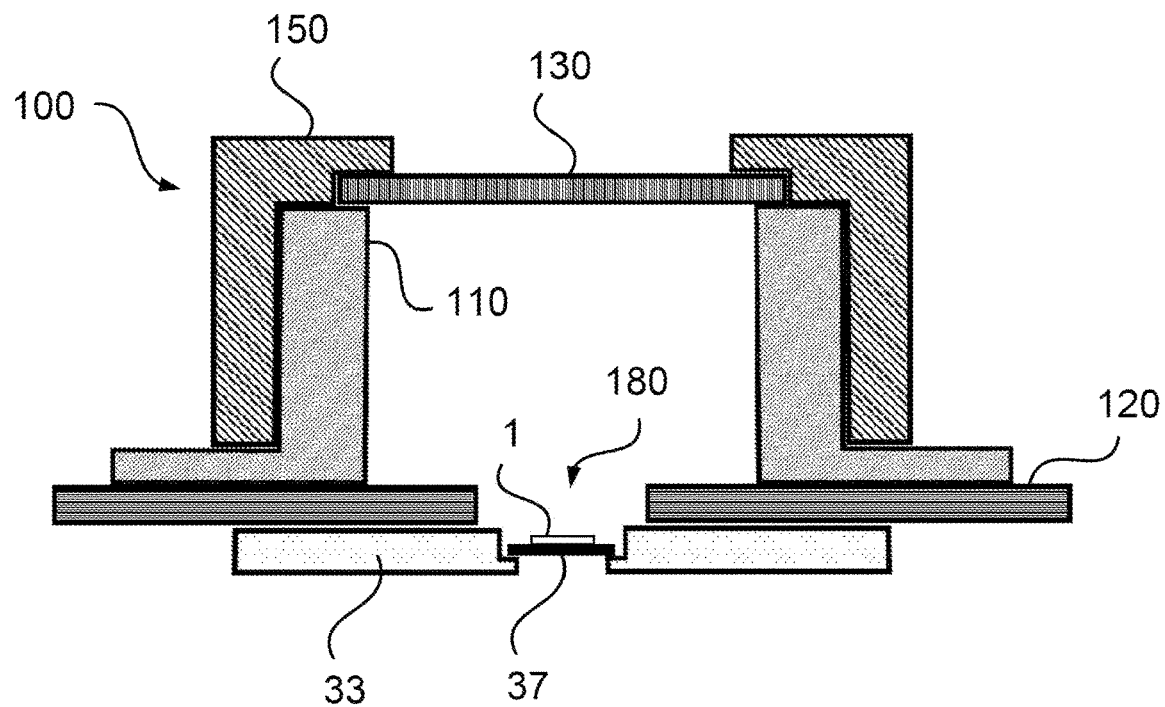
FIG. 4 illustrates an incubation chamber for incubating a sample according to an embodiment of the present disclosure in a simplified sectional view.

FIG. 4 illustrates an incubation chamber for incubating a sample according to an embodiment of the present disclosure (or a "first set of embodiments" as explained before in more detail) in a simplified sectional view.

The elements of the incubation chamber 100 shown in FIG. 4 are designed slightly differently from the incubation chamber 900 as shown in FIG. 1, but may likewise be designed in the same manner. The present disclosure is not characterized in or limited by specific parts of the incubation chamber 900 being present or not. Elements of the incubation chamber 100 shown in FIG. 4 are designated with identical reference numerals as for the incubation chamber 900 shown in FIG. 1.

Also here, for assembling the incubation chamber 100 shown in FIG. 4, an open silicone cylinder 110 is mounted to a glass plate forming a bottom 120 of the incubation chamber. The cylinder 110 is again closed by a glass lid 130. The whole assembly is, in the incubation chamber 100, covered by a metal cover 150 which fixes the glass lid 130 and no separate glass window 160 is provided. The gas to which the sample 1 is to be exposed may be provided and the gas atmosphere may be maintained in any manner conceivable.

A middle plate 33, e.g. as previously explained in connection with FIGS. 2 and 3, is attached to a lower surface of the bottom 120 of the incubation chamber 100 by using any means conceivable, such as mechanical and magnetic attachment means not specifically shown for reasons of generality, and the middle plate 33 is detachable from the incubation chamber 100 by effecting a movement of the incubation chamber 100 as described hereinbefore in full detail for different embodiments. As shown the middle plate 33 is provided in an opened state, i.e. with only a lower enclosing element 37 being inserted, and the sample 1 is provided on the lower enclosing element. The bottom 120 of the incubation chamber 100 comprises an opening 180 for providing fluid access to the opening 36 of the middle plate 33.

Figure 5:
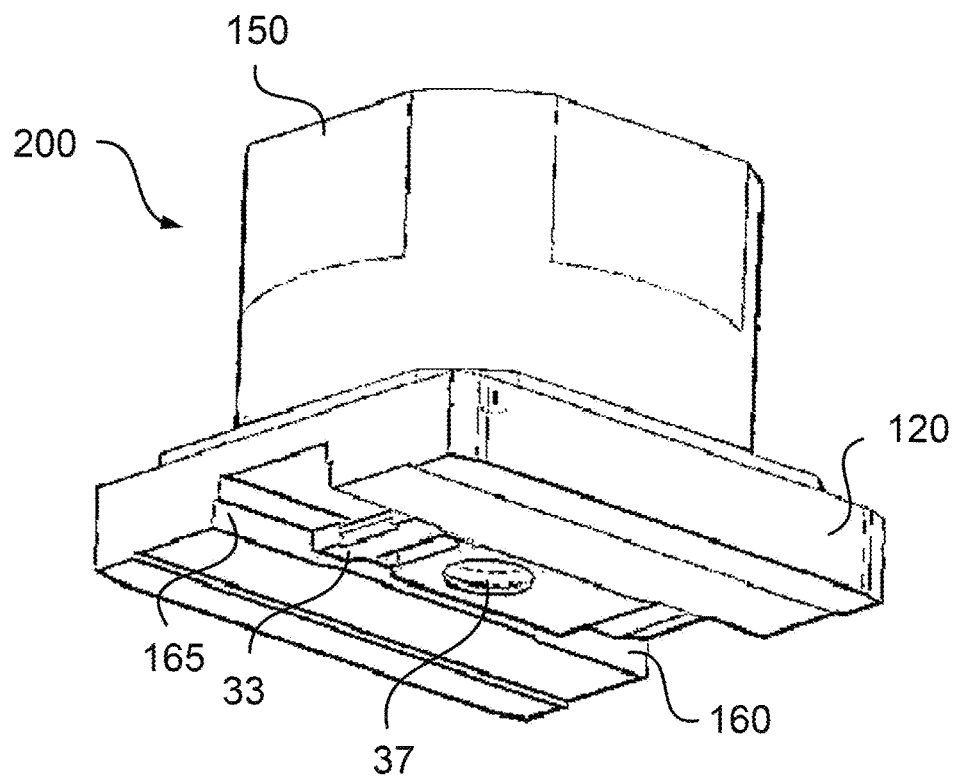
FIG. 5 illustrates an incubation chamber for incubating a sample according to an embodiment of the present disclosure in a simplified perspective view.

FIG. 5 illustrates an incubation chamber for incubating a sample according to a further embodiment (or a "second set of embodiments" as explained before in more detail) of the present disclosure in a simplified perspective view. The elements of the incubation chamber 200 shown in FIG. 5 may again be designed slightly differently from the incubation chamber 900 as shown in FIG. 1 or the incubation chamber 100 shown in FIG. 4, but may likewise be designed in the same manner. Elements of the incubation chamber 200 shown in FIG. 5 are designated with identical reference numerals as for the incubation chambers 900 and 100 as shown in FIGS. 1 and 4.

In the incubation chamber 200 shown in FIG. 5, a bottom 120 of the incubation chamber 200 comprises an elongated opening 160 with a guiding structure 165 adapted to slidingly receive the middle plate 33. As mentioned, this may be a dovetail structure or any other guiding structure being suitable to hold the middle plate 33. The middle plate 33 is, in the incubation chamber 200, detachable from the incubation chamber 200 by effecting a movement in the form of a linear movement defined by said guiding structure 165, i.e. particularly in parallel to a longitudinal extension of the guiding structure 165, and an engagement structure, as further described in detail below, comprises a stop to hold the middle plate 33 in place while effecting said movement as, e.g., shown later on in FIGS. 8B, 8D, and 8E with the reference number 21. Again, the bottom 120 of the incubation chamber 200 comprises an opening for providing fluid access to the opening 36 of the middle plate 33 which is not visible in FIG. 5, however, as being covered by the middle plate 33.

Figure 6A:
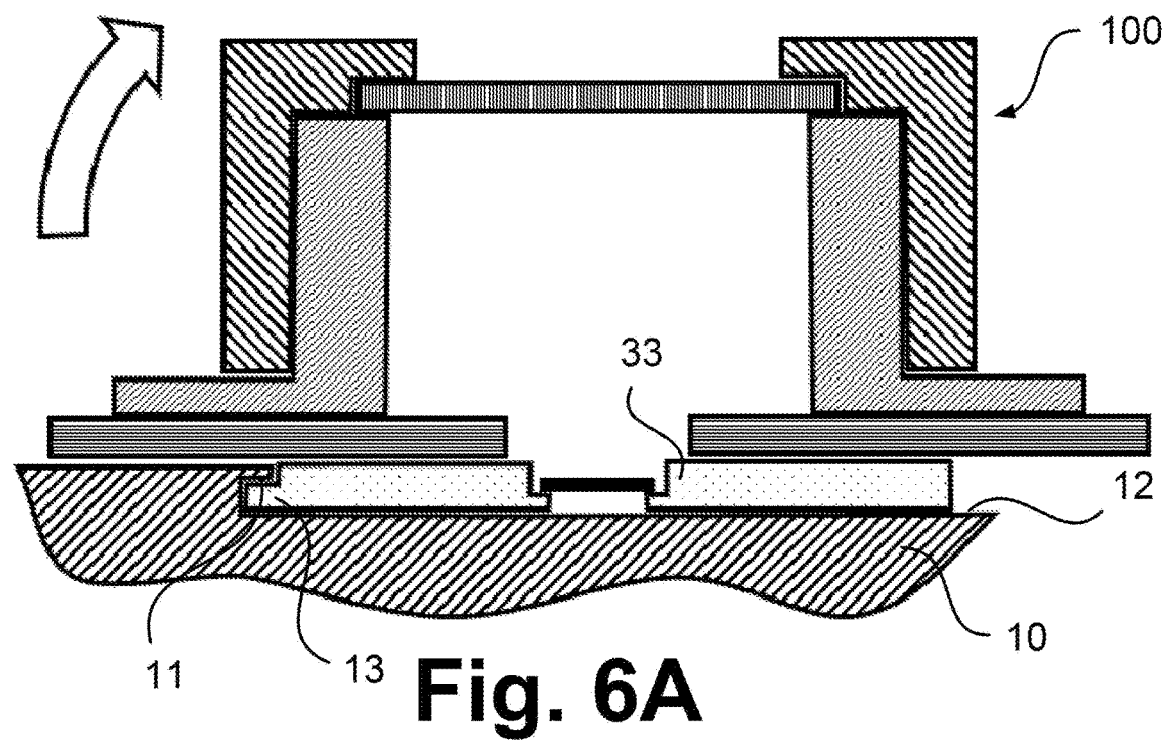
FIGS. 6A and 6B illustrate steps of detaching a middle plate from an incubation chamber by tilting according to an embodiment of the present disclosure.
Figure 6B:
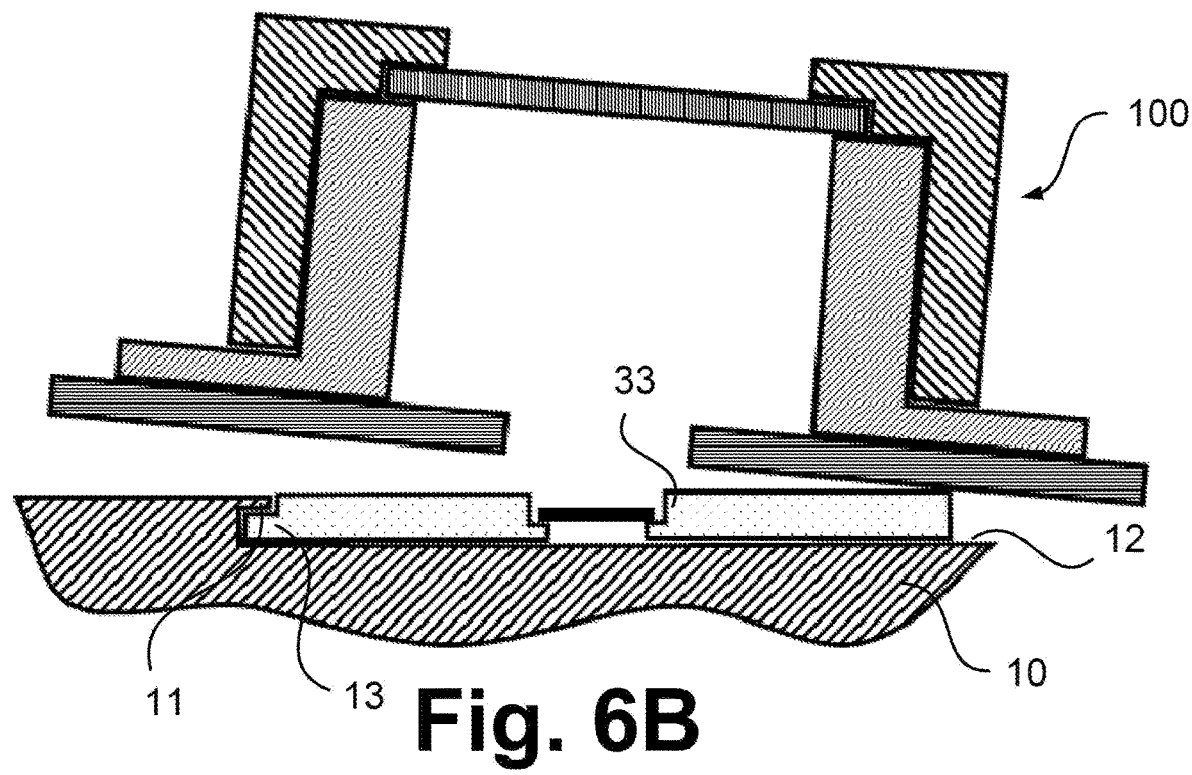

FIGS. 6A and 6B illustrate steps of detaching a middle plate from an incubation chamber by tilting according to an embodiment of the present disclosure. The incubation chamber is embodied essentially as described for the embodiment (or "first group of embodiments") shown in FIG. 4 and is therefore designated 100.

In general, as the middle plate 33 protrudes from the bottom 120 of the incubation chamber 100 when attached thereto, an engagement structure 11 may be provided as a recess with a shape complementary to at least a part of a shape of the middle plate which is adapted to receive at least a part of the middle plate 33 protruding from the bottom 120 of the incubation chamber 100. In the specific embodiment shown, in order to restrict a tilting movement, the engagement structure 11 is provided as a structure with an undercut into which a corresponding protrusion 13 provided at the middle plate 33 may be inserted, such that when tilting the incubation chamber 100 while maintaining the protrusion 13 of the middle plate 33 inserted into the undercut, as indicated with a white arrow in FIG. 6A, an overhang of the undercut "pulls off" the middle plate 33.

Figure 7A:
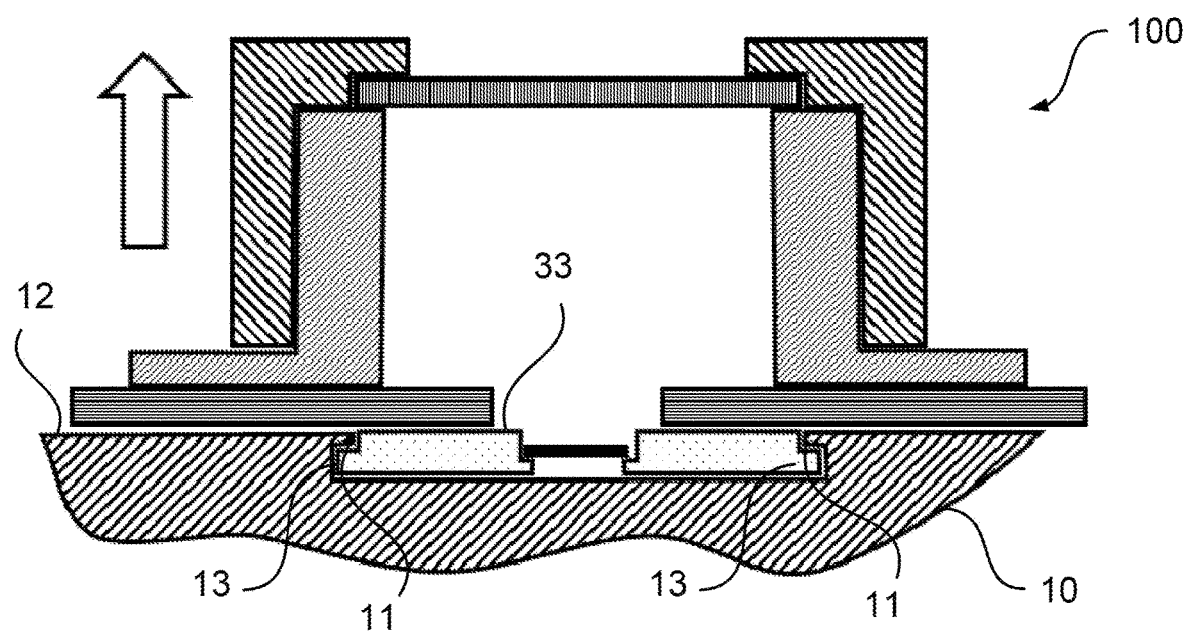
FIGS. 7A and 7B illustrate steps of detaching a middle plate from an incubation chamber by lifting according to an embodiment of the present disclosure.
Figure 7B:
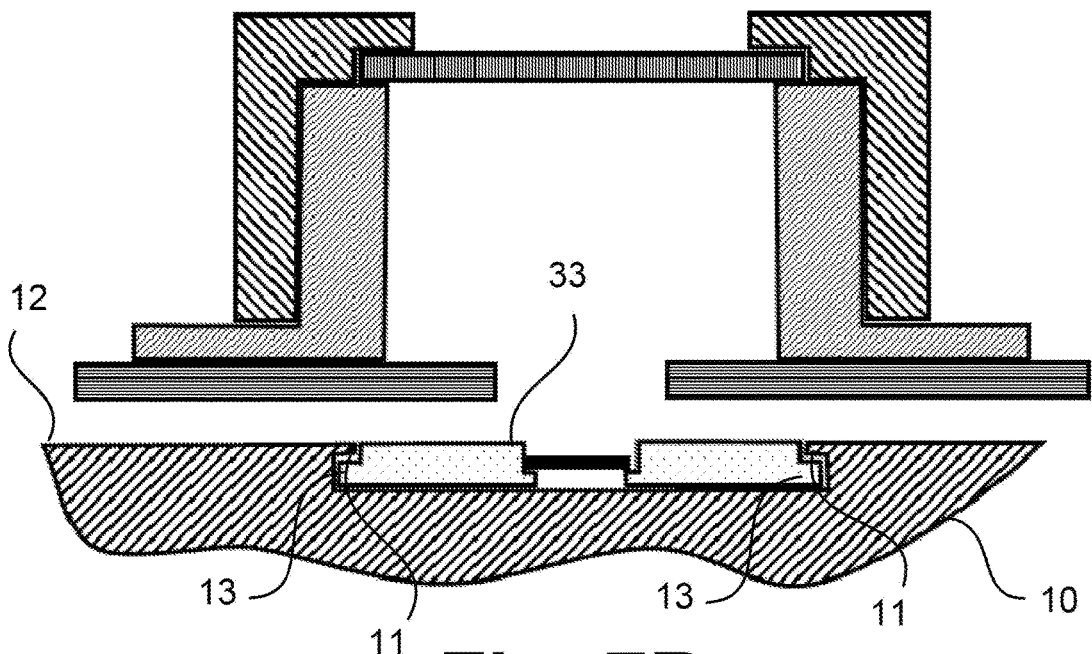

FIGS. 7A and 7B illustrate steps of detaching a middle plate from an incubation chamber by lifting according to an embodiment of the present disclosure. Also here, the incubation chamber is embodied essentially as described for the embodiment (or "first group of embodiments") shown in FIG. 4 and is therefore designated 100.

Also here, in general, as the middle plate 33 protrudes from the bottom 120 of the incubation chamber 100 when attached thereto, an engagement structure 11 may be provided as a recess with a shape complementary to at least a part of a shape of the middle plate which is adapted to receive at least a part of the middle plate 33 protruding from the bottom 120 of the incubation chamber 100.

A lifting movement may specifically be restricted by providing a parallel set of guiding elements with undercuts as the engagement structure 11, e.g. in the form of a dovetail guide, which are adapted to slidingly receive complementary structures provided at the middle plate in the form of protrusions 13 in an insertion direction which is, in the illustration of FIGS. 7A and 7B, orthogonal to the paper plane. When lifting the incubation chamber 100 in a direction at an angle to the insertion direction, as indicated with a white arrow according to FIG. 7A, the middle plate 33 may be detached from the incubation chamber 100.

In FIGS. 6A to 7B, as well as in the Figures below, a device provided according to the present disclosure is shown in a partial view and is indicated 10. The device 10 can, as mentioned before, be a high-pressure freezing device adapted to perform all or at least a part of the further steps of high-pressure freezing as well, or the device 10 may be a dedicated device separate from a high-pressure freezing device, i.e. a separate constructional unit. The device 10 according to FIGS. 6A to 7B comprises the engagement structure 11 while the device 10 according to the subsequent Figures comprises an engagement structure 21. A surface of the device 10 is indicated 12.

FIGS. 8A to 8E illustrate steps of detaching a middle plate from an incubation chamber by sliding and of sealing the opening in the middle plate according to an embodiment of the present disclosure.

The incubation chamber is, in contrast to FIGS. 6A to 7B, embodied essentially as described for the embodiment (or "second group of embodiments") shown in FIG. 5 and is therefore designated 200 here as well.

Figure 8A:
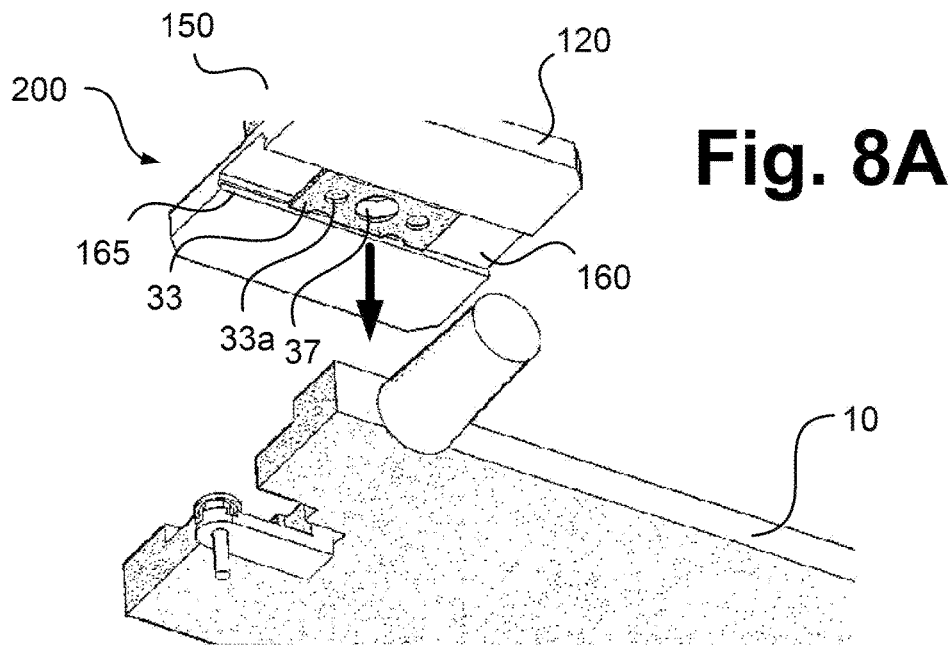
Figure 8B:
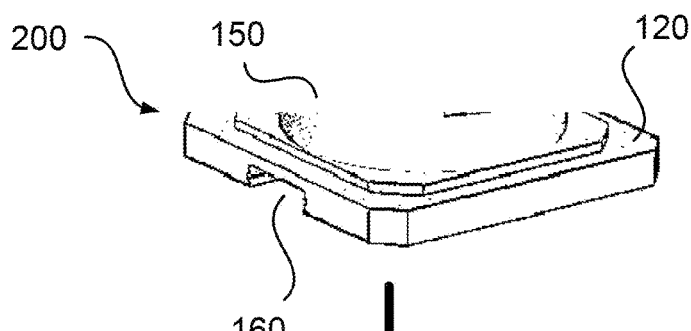
Figure 8B:
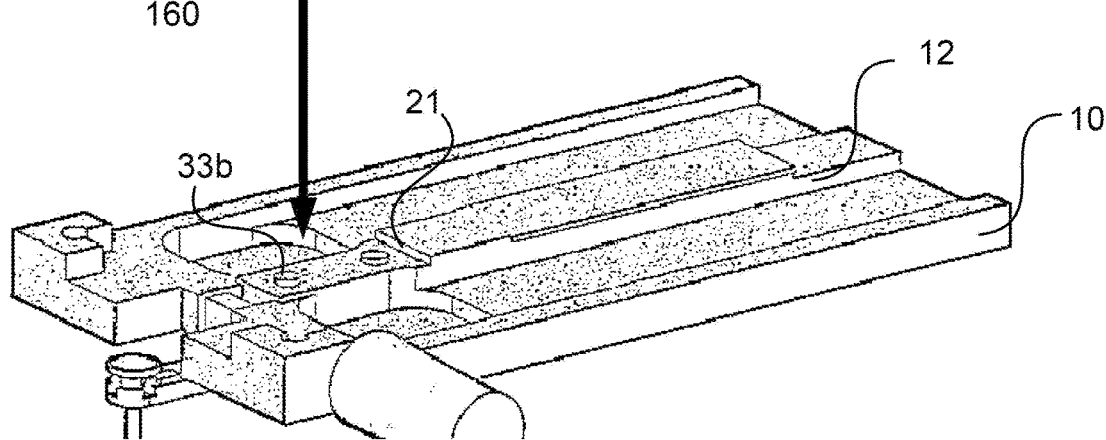

As in the incubation chamber 200 the bottom 120 comprises an opening 160 with a guiding structure 165 adapted to slidingly receive the middle plate 33, and as the middle plate 33 is detachable from the incubation chamber 200 by effecting a movement in the form of a linear movement defined by said guiding structure 165, the engagement structure 21 may be provided as a stop to hold the middle plate 33 in place while effecting said movement. In order to guide the incubation chamber 200 in this movement, a rail structure 12 may be provided in the manner shown or in a similar design. FIGS. 8A and 8B show two perspectives showing the underside of the incubation chamber 200 and of the device 10 (FIG. 8A) and the top side of the incubation chamber 200 and of device 10 (FIG. 8B). As symbolized with an arrow, the incubation chamber 200 with the middle plate 33 attached thereto may be placed onto the device 10. As also shown in FIGS. 8A and 8B, matching protrusions and recesses 33a, 33b may be provided in order to improve a proper alignment of the middle plate 33 and the device 10.

Figure 8C:
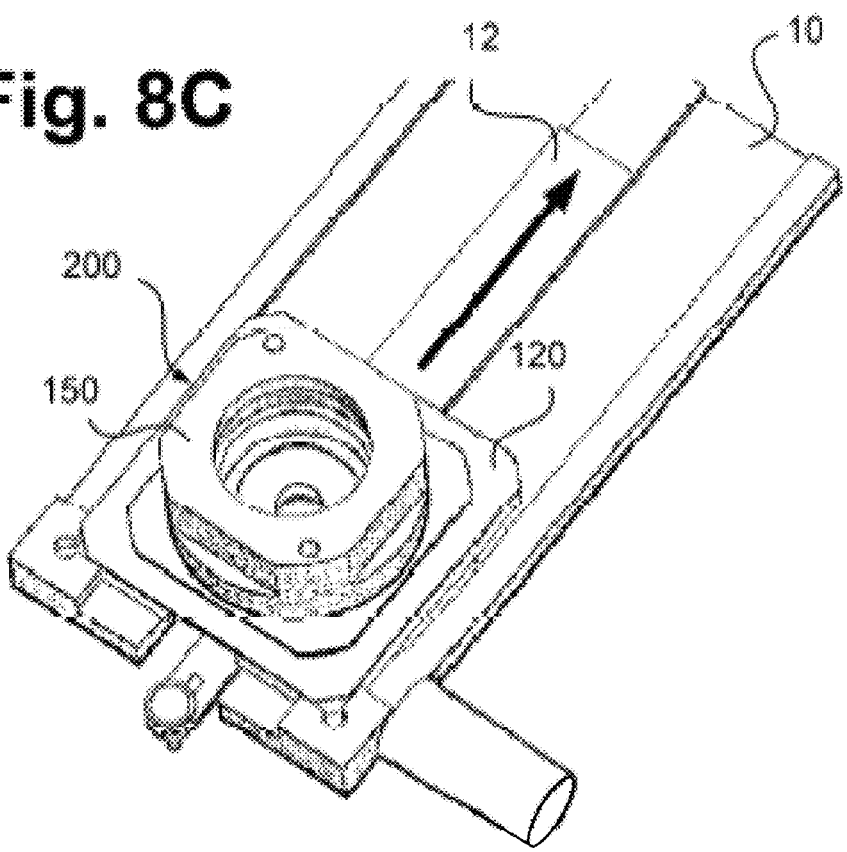

FIG. 8C shows, as also symbolized with an arrow, a movement performed in order to detach the middle plate 33 from the incubation chamber 200.

Figure 8D:
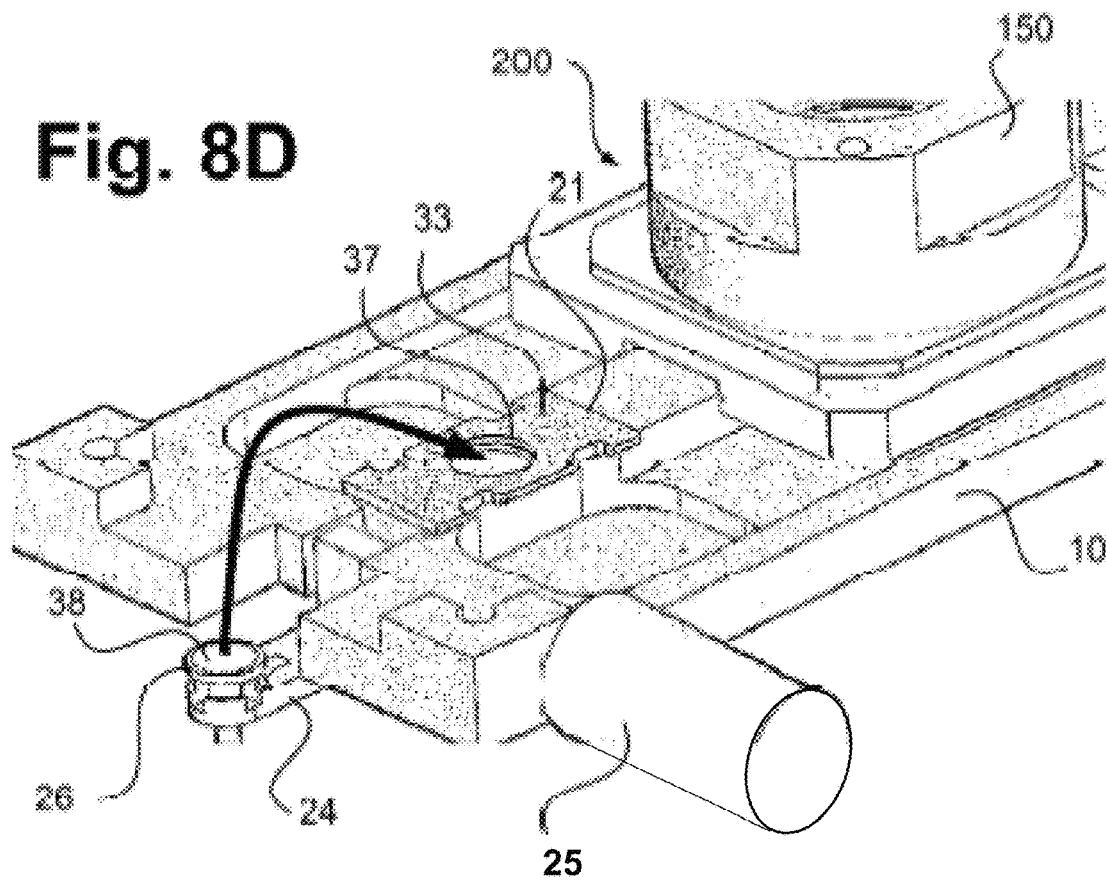

As shown in FIG. 8D, the device 10 is adapted to hold the middle plate 33 detached from the incubation chamber 200 in place at a processing position, as defined by the engagement structure 21, and the device 10 comprises a pivoting arm 24 with a receptacle 26 adapted to receive a further (top) enclosing element 38 to be fitted into the opening 36 of the middle plate 33, such as to enclose the sample 1 therein. The pivoting arm 24 is pivotable, as indicated by an arrow in FIG. 8C, between a loading position wherein the further enclosing element 38 is insertable into the receptacle 26 of the pivoting arm 24, and a inserting position in which the further enclosing element 38 in the receptacle 26 of the pivoting arm 24 is placed in the opening 36 of the middle plate 33 held in place at the processing position. For pivoting the pivoting arm 24, a knob 25 may be provided. FIG. 8E shows, again symbolized with an arrow, how the middle plate 33 can be removed from the device 10 after the further enclosing element 38 has been placed into the opening 36 and the pivoting arm 24 was swung back to the loading position.

What is claimed is:

1. A device for preparing a microscopic sample for a high-pressure freezing process in which the sample is provided using an arrangement comprising a middle plate of a high-pressure freezing cartridge and an incubation chamber, the middle plate being attached to the incubation chamber and being detachable from the incubation chamber by effecting a relative movement between the middle plate and the incubation chamber, and the sample being provided on an enclosing element which is fitted into an opening of the middle plate, wherein the device comprises an engagement structure adapted to engage with the middle plate and to restrict a movement of the middle plate while the incubation chamber is moved, such as to effect said relative movement between the middle plate and the incubation chamber and to thereby detach the middle plate from the incubation chamber.

2. The device according to claim 1, wherein the device is adapted to hold the middle plate detached from the incubation chamber in place at a processing position, and wherein the device comprises a pivoting arm including a receptacle adapted to receive a further enclosing element to be fitted into the opening of the middle plate, such as to enclose the sample therein, wherein the pivoting arm is pivotable between a loading position wherein the further enclosing element is insertable into the receptacle of the pivoting arm and an inserting position in which the further enclosing element in the receptacle of the pivoting arm is placed in the opening of the middle plate held in place at the processing position.

3. The device according to claim 2, wherein the receptacle is adapted to adhesively hold the further enclosing element.

4. The device according to claim 1, wherein the middle plate is attached to a lower surface of a bottom of the incubation chamber by at least one of mechanical and magnetic attachment means, wherein the middle plate is detachable from the incubation chamber by effecting said relative movement in the form of at least one of (i) a linear movement of the incubation chamber in a plane corresponding to the lower surface of the bottom of the incubation chamber, (ii) a rotational movement of the incubation chamber in the plane corresponding to the lower surface of the bottom of the incubation chamber, (iii) a tilting movement of the incubation chamber around an axis parallel to the lower surface of the bottom of the incubation chamber, and (iv) a lifting movement of the incubation chamber in a direction at an angle to the lower surface of the bottom of the incubation chamber, and wherein the engagement structure is adapted to engage with the middle plate to restrict said at least one of a linear movement, rotational movement, tilting movement, and lifting movement.

5. The device according to claim 4, wherein the middle plate protrudes from the bottom of the incubation chamber when attached to the bottom of the incubation chamber, and wherein the engagement structure includes a recess having a shape complementary to at least a part of a shape of the middle plate and is adapted to receive at least a part of the middle plate protruding from the bottom of the incubation chamber.

6. The device according to claim 1, wherein a bottom of the incubation chamber comprises an opening having a guiding structure adapted to slidingly receive the middle plate, wherein the middle plate is detachable from the incubation chamber by effecting said relative movement in the form of a linear movement defined by said guiding structure and wherein the engagement structure comprises a stop to hold the middle plate in place while effecting said relative movement.

7. An incubation chamber adapted to be used in an arrangement comprising the incubation chamber and a middle plate of a high-pressure freezing cartridge, the incubation chamber comprising means to attach the middle plate to the incubation chamber such that the middle plate is detachable from the incubation chamber by effecting a relative movement between the middle plate and the incubation chamber.

8. A middle plate of a high-pressure freezing cartridge adapted to be used in an arrangement comprising an incubation chamber and the middle plate, the middle plate comprising means to attach the middle plate to the incubation chamber such that the middle plate is detachable from the incubation chamber by effecting a relative movement between the middle plate and the incubation chamber.

9. An apparatus comprising:
an incubation chamber; and
a middle plate of a high-pressure freezing cartridge;
wherein one of the incubation chamber and the middle plate comprises attachment means for attaching the middle plate to the incubation chamber such that the middle plate is detachable from the incubation chamber by effecting a relative movement between the middle plate and the incubation chamber.

10. A method for preparing a microscopic sample for a high-pressure freezing process, the method comprising:
providing an incubation chamber;
providing a middle plate of a high-pressure freezing cartridge, the middle plate being attached to the incubation chamber and being detachable from the incubation chamber by effecting a relative movement between the middle plate and the incubation chamber, the middle plate having an opening and an enclosing element fitted into the opening;
providing a device comprising an engagement structure adapted to engage with the middle plate and to restrict a movement of the middle plate while the incubation chamber is moved;
arranging the sample on the enclosing element of the middle plate;
engaging the engagement structure with the middle plate; and
effecting said relative movement between the middle plate and the incubation chamber, thereby detaching the middle plate from the incubation chamber.

11. The method according to claim 10, wherein said device is adapted to hold the middle plate detached from the incubation chamber in place at a processing position, and wherein the device comprises a pivoting arm with a receptacle adapted to receive a further enclosing element to be fitted into the opening of the middle plate, such as to enclose the sample, wherein the pivoting arm is pivotable between a loading position wherein the further enclosing element is insertable into the receptacle of the pivoting arm and an inserting position wherein the further enclosing element inserted in the receptacle of the pivoting arm is placeable in the opening of the middle plate held in place at the processing position, and wherein said method further comprises holding the middle plate detached from the incubation chamber in place at the processing position and inserting the further enclosing element using the pivoting arm of the device.

12. The method according to claim 10, wherein the sample is living matter, and the method further comprises exposing the sample to defined environmental conditions provided in the incubation chamber.

* * * * *